United States Patent
Vogele

(10) Patent No.: US 9,622,829 B2
(45) Date of Patent: Apr. 18, 2017

(54) IMMOBILIZATION DEVICE

(75) Inventor: Michael Vogele, Schwabmunchen (DE)

(73) Assignee: ISYS MEDIZINTECHNIK GMBH, Kitzbuhel (AT)

( * ) Notice: Subject to any disclaimer, the term of this patent is extended or adjusted under 35 U.S.C. 154(b) by 675 days.

(21) Appl. No.: 13/226,407

(22) Filed: Sep. 6, 2011

(65) Prior Publication Data

US 2012/0266898 A1 Oct. 25, 2012

(30) Foreign Application Priority Data

Apr. 21, 2011 (DE) .................... 20 2011 005 573 U

(51) Int. Cl.

| A61B 90/11 | (2016.01) |
| A61B 90/17 | (2016.01) |
| A61B 90/14 | (2016.01) |
| A61B 6/04 | (2006.01) |
| A61B 17/00 | (2006.01) |
| A61B 17/34 | (2006.01) |
| A61B 90/00 | (2016.01) |

(52) U.S. Cl.
CPC .............. *A61B 90/17* (2016.02); *A61B 90/14* (2016.02); *A61B 6/0428* (2013.01); *A61B 6/0492* (2013.01); *A61B 90/39* (2016.02); *A61B 2017/00566* (2013.01); *A61B 2017/00951* (2013.01); *A61B 2017/3407* (2013.01); *A61B 2090/064* (2016.02); *A61B 2090/3983* (2016.02); *A61B 2090/3991* (2016.02)

(58) Field of Classification Search
CPC .................................... A61B 19/203
USPC .... 128/869, 879; 5/621, 622, 625, 628, 627, 5/600, 601, 623; 600/37, 16, 201, 18, 600/210, 427; 606/201, 121, 190, 191, 606/192, 170, 185; 601/24, 11, 6, 43, 44
See application file for complete search history.

(56) References Cited

U.S. PATENT DOCUMENTS

| 3,745,998 | A | * | 7/1973 | Rose ................................. 602/6 |
| 4,039,705 | A | * | 8/1977 | Douek ........................ C09J 4/06 156/331.7 |
| 5,632,758 | A | * | 5/1997 | Sklar ................ A61B 17/32001 606/1 |
| 5,945,827 | A | * | 8/1999 | Gronauer ............. A61B 5/0555 324/318 |
| 6,210,323 | B1 | * | 4/2001 | Gilhuly .................. A61B 17/02 600/208 |
| 6,371,906 | B1 | * | 4/2002 | Borst ..................... A61B 17/02 128/857 |
| 6,530,941 | B1 | * | 3/2003 | Muller ................ A61B 6/0421 601/24 |
| 6,558,314 | B1 | * | 5/2003 | Adelman et al. ............... 600/37 |

(Continued)

*Primary Examiner* — Tarla Patel
(74) *Attorney, Agent, or Firm* — Venable LLP; Michele V. Frank

(57) ABSTRACT

A device for immobilizing a patient for a medical test or operation includes a molding element that is convertible from a flexible, elastic form to a rigid form by the application of a vacuum. The molding element is attached to the patient by an elastic layer while in the flexible, elastic form where it conforms to the contours of the patient's body. Then the molding element is converted to its rigid form thereby immobilizing the patient. Auxiliary devices can be attached to the immobilizing device and these devices, such as a pivot arm suspension can be used to fix the immobilized patient to an operating table.

10 Claims, 4 Drawing Sheets

(56) References Cited

U.S. PATENT DOCUMENTS

| | | | | |
|---|---|---|---|---|
| 6,589,166 | B2* | 7/2003 | Knight | A61B 17/02 600/205 |
| 7,479,104 | B2* | 1/2009 | Lau et al. | 600/37 |
| 2003/0078470 | A1* | 4/2003 | Borst | A61B 17/02 600/37 |
| 2006/0041206 | A1* | 2/2006 | Schaffrath | A61B 90/36 601/6 |
| 2007/0004993 | A1* | 1/2007 | Coppens | A61F 5/0104 602/7 |
| 2007/0191743 | A1* | 8/2007 | McBean et al. | 601/5 |
| 2008/0230074 | A1* | 9/2008 | Zheng | A61B 6/04 128/869 |

* cited by examiner

IMMOBILIZATION DEVICE

CROSS-REFERENCE TO PRIOR APPLICATIONS

This application claims the priority of German Utility Model Application No. 20 2011 005 573.6, filed 21 Apr. 2011.

U.S. GOVERNMENT SUPPORT

Not Applicable

AREA OF THE INVENTION

The invention relates to a device for reliable immobilization of the human body or parts of the human body, in such uses as medical target devices, markers, and/or surgical instruments for image-guided, minimally invasive operating methods being fixed reliably. "Immobilization" is to be understood in this case in the medical meaning as also including the fixing in place, splinting, positioning, repositioning, compression, or casting of the human body.

DESCRIPTION OF THE BACKGROUND OF THE INVENTION

In many fields of human medicine or medical research, secure fixing/immobilization/splinting or compression and/or molding of the patient or parts of the patient or the (mechanical) attachment of devices or appliances is necessary. This is of particularly great significance not only in the field of diagnostic and therapeutic radiology, radiation therapy, or in the case of operative/surgical interventions (neurosurgery, ENT, orthopedics, etc.), but also in the pre-operative or postoperative care of wounds/injuries.

Through the incorporation of computer technology in diagnosis and therapy, the requirements have risen for the precision and reproducibility both during the fixing of a stereotactic frame system onto a patient and also during the immobilization of the body itself. Comfort, rapid application, mobility, and cost are significant advantages of the present invention.

The following types of immobilization are known as the prior art:

a) Immobilization of the body using bands or cuffs: In this case, the body of the patient lies on a foam underlay and bands are stretched transversely over the body to immobilize the patient onto the underlay. However, the following points are some of the disadvantages of this approach:

Pressure points, shifting, and/or skin swelling can occur due to strong tension of the bands (non-homogeneous pressure distribution);

After removal of the retaining elements (bands), repeated immobilization in precisely the same location is virtually impossible, which is disadvantageous in particular in the case of stereotactic operations and in radiation therapy;

The body is not sufficiently fixed; particularly in the lateral direction; position cannot be restricted or defined sufficiently.

b) Immobilization of the body by screw connections to the bones: The body of the patient is screwed at multiple points to a metal frame. The following points are disadvantageous in this case:

The screw connection to the bone represents an invasive method and is therefore only possible and justified in the case of specific indications;

The mental stress of the patient is substantial;

The method is only applicable to specific mountings of the patient and obstructs medical operations;

Immobilization of the soft tissue parts (muscles, ligaments, connective tissue) is practically impossible.

c) Immobilization by formwork: In this case, the patient is laid on a type of "air mattress", which is filled with foam beads. Upon suctioning out the air from this mattress, it solidifies by pressing the foam beads against one another. The vacuum mattress is initially adapted in the first step and then suctioned out further in the second step. An imprint of the body is obtained by this method. In this method, it is disadvantageous that:

The typically used "mattresses" restrict patient motion, but do not result in actual immobilization;

The body is solely held in position by gravity or by compression bands, so that no fixed connection exists between the surfaces;

In the case of uncooperative patients, sufficient immobilization is practically impossible;

Precise molding is also not possible, since in practice the mattress cannot be applied precisely to all body parts;

Pressure points often arise due to wrinkling or excessively strong contact pressure, which can result in tissue injuries particularly in sedated patients.

d) Vacuum fixation system: In vacuum fixation systems, the molding element is applied to the body via vacuum. By suctioning out the air between the molding element and patient surface, a good connection for molding and fixation can be provided. In this case, it is disadvantageous that:

A vacuum pump must run continuously, so that the connection between molding element and patient is maintained;

The system is complex, not easy to handle, and difficult to transport;

In the case of interventions which require a high level of asepsis or even sterility, the air stream of the vacuum pump represents a hazard (bacteria entrainment);

Higher connecting forces and therefore improved molding and immobilization are not possible, because injuries (e.g., reduced blood perfusion, effusion of blood) may arise due to excessively high and long-lasting pressures;

In the event of failure of the vacuum, the connection is lost. This is critical in particular if, for example, a hazard to life and limb of the patient can arise or the (surgical/radiological) intervention must be terminated or interrupted in the event of loss of the connection;

The method is complex overall and is hardly practicable in particular for radiological/surgical interventions.

Other techniques such as splints, thermoplastic material, plastic imprint, plaster casts, etc., have similar disadvantages. In addition, these methods also entail substantial financial or chronological outlay and are therefore only used for long-term applications.

SUMMARY OF THE INVENTION

The invention is therefore based on the object of providing a device for immobilization which avoids the aforementioned disadvantages, is simple in construction and application, and therefore protects the patient to a high degree. The device additionally allows the exact attachment of calibration points (so-called markers) and optimum accessibility to operation regions.

An essential feature in this case is an adhesive layer, by which stable "gluing" of the molding element onto the human body is made possible. This can be achieved using a spray adhesive or an adhesive film, so that after a cover band is pulled off, it is possible to press or "model" on the adhesive layer. The molding element is still soft, so that exact adaptation can occur. The molding element is only solidified and "hardened" into a dimensionally-stable molding element having stable form after application of vacuum thereto.

By means of a locking a pivot arm, the immobilized body can be additionally fixed in relation to the baseplate of an intervention or operating table, a compression of the body being achieved—if desired—by light pressure. A preferred baseplate, a carbon adapter plate attached to the molding element is x-ray transparent and increases the stability of the entire device through the high stiffness.

After completing immobilization and application of a sterile covering, a medical intervention (i.e., an operation) (optionally having robot support) can occur in the operating room window, for example. The robot is preferably mechanically coupled to the molding element via the baseplate, i.e., geometrically fixed. Alternatively, a mini-robot can also be directly attached on the molding element, e.g., via a carbon adapter plate. Markers for imaging methods or navigation can also be reproducibly attached. Since it is not simple gluing at spots, but rather a large-area, ergonomic adhesion of an additionally flexible, then rigid molding element, maximum surface contact with high retention forces at maximum comfort results.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a device for immobilization of the human body for medical and related applications.

Figure 2:
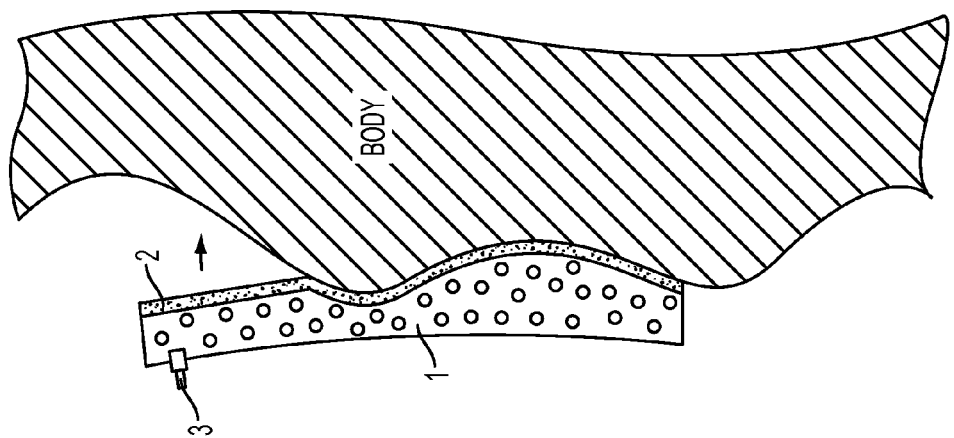
FIG. 2 is a diagram showing the second step in the attachment of the device for immobilization.
Figure 1:
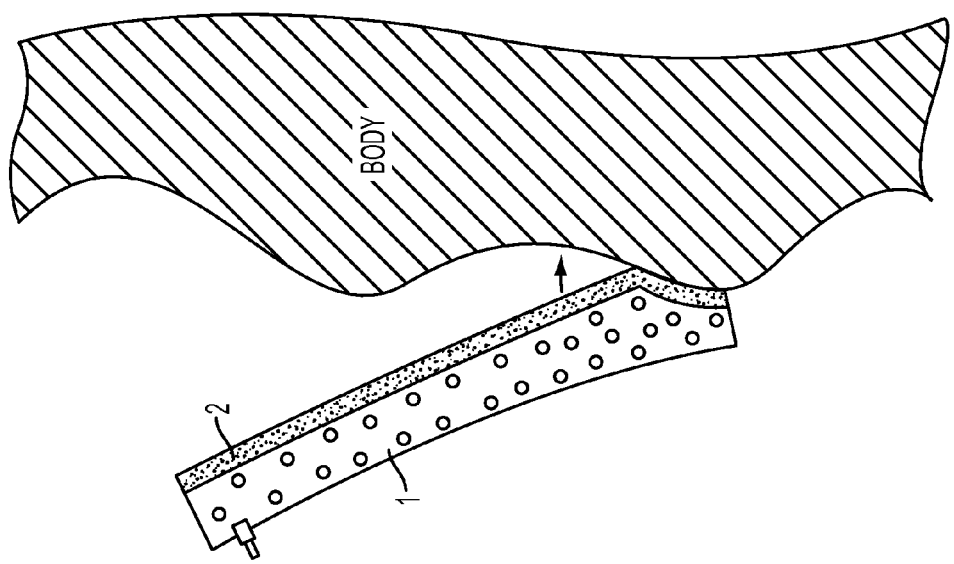
FIG. 1 is a diagram showing the first step in the attachment of the device for immobilization.
Figure 3:
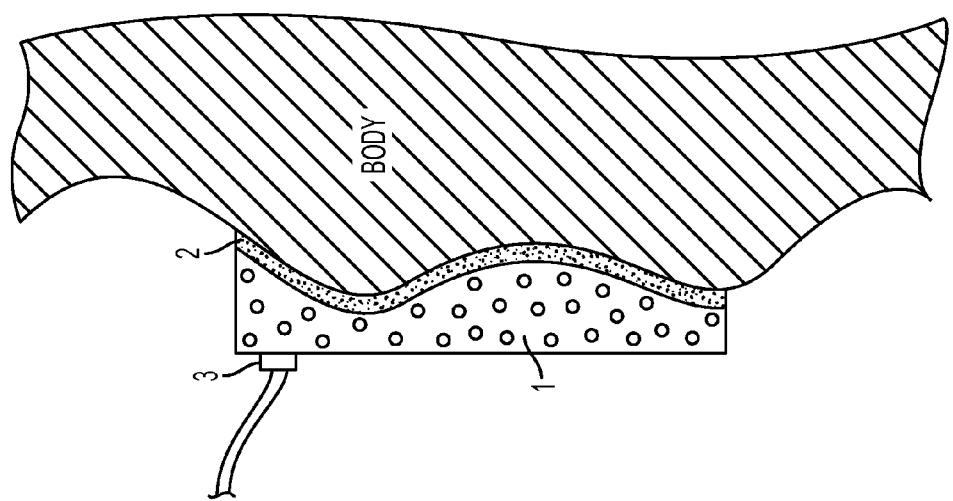
FIG. 3 is a diagram showing the third step in the attachment of the device for immobilization.
Figure 6:
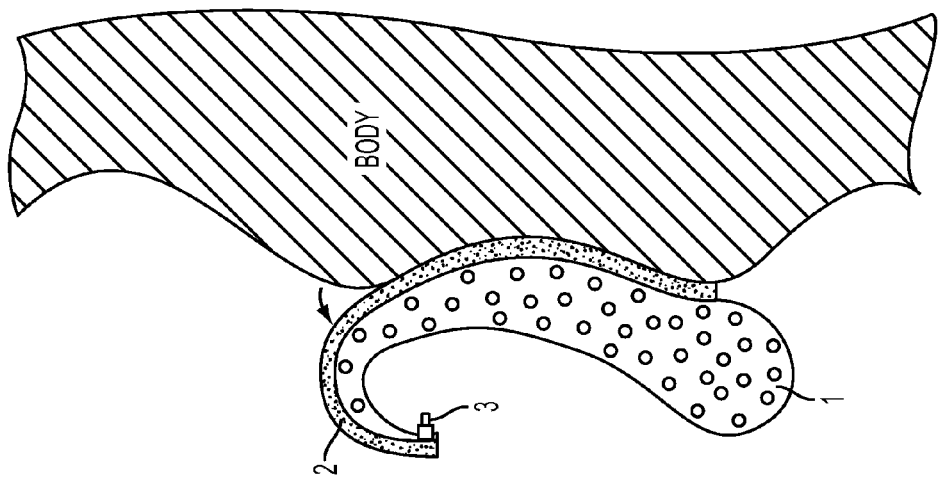
FIG. 6 is a diagram showing the second step in the removal of the device for immobilization.
Figure 5:
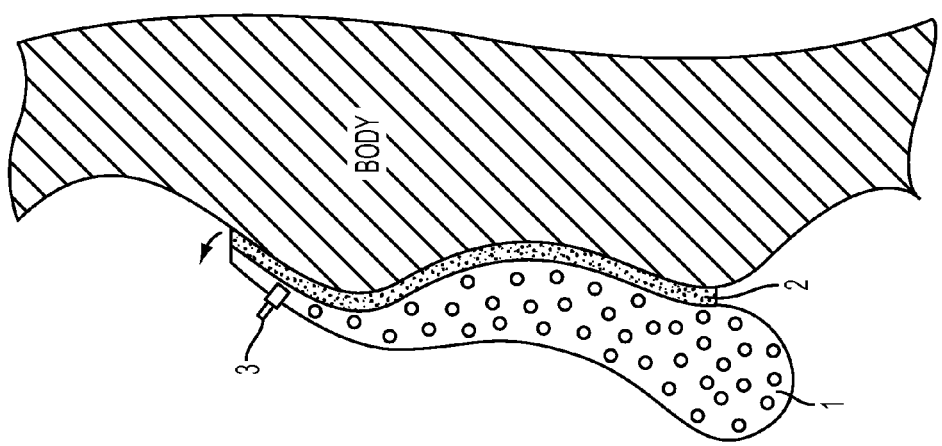
FIG. 5 is a diagram showing the first step in the removal of the device for immobilization.

The device for fixation of the human body or of body parts comprises a molding element 1, which is positionable on the body surface (shown shaded; a back part here, for example) (FIG. 1). This is performed using an adhesive layer 2, which is connected to the molding element 1, e.g., an inner adhesive film is glued on and optionally has a carrier layer to an outer adhesive film, which is pressed against the skin of the body. The adhesive layer 2 can also be formed by a spray adhesive, which is sprayed onto the skin and/or the body-side surface of the molding element 1. As is obvious from FIG. 2, the molding element 1 is then pressed on and glued along the spinal column (in this example). As shown in FIG. 3 a vacuum pump is then connected to a vacuum valve 3 and the "cushion" molding element 1 is evacuated. The beads in the molding element 1 therefore press closely against one another and thus form a "hard", dimensionally-stable shell. In this position, the molding element 1 may not be removed, but rather adheres with high retention force on the back or in the shoulder area of the body. The molding element 1 may only be peeled off again after the vacuum therein is canceled, as schematically shown in FIGS. 5 and 6. The molding element 1 may thus be returned from the dimensionally-stable fixation state back into a soft, moldable state.

Figure 4:
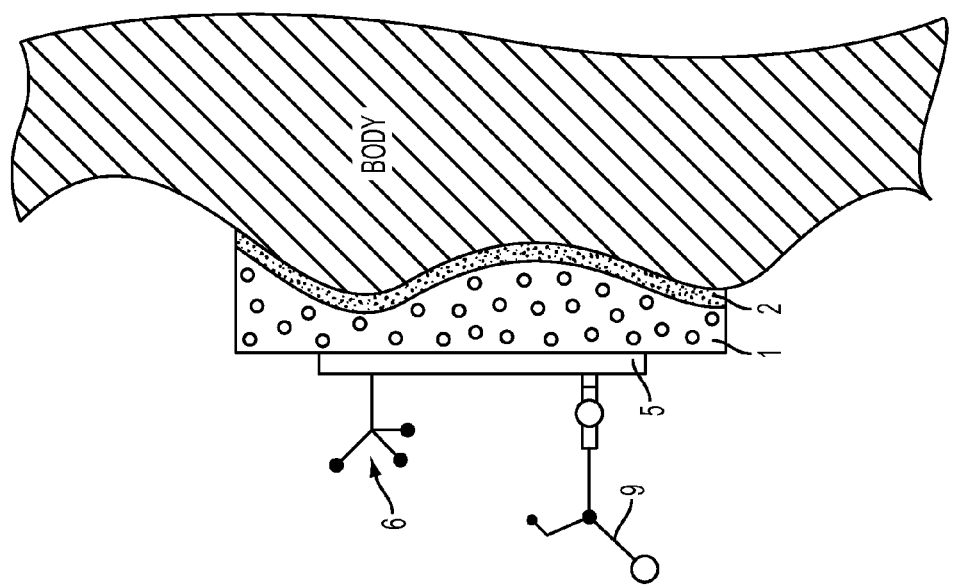
FIG. 4 is a diagram showing the placement of additional components onto the device for immobilization.

The envelope of the molding element 1 is implemented like a fabric or film and is filled using granules, in particular plastic beads. The molding element 1 is implemented as elastic to press against the body in the attachment direction and has high tensile strength in the transverse direction. As shown in FIG. 4, an adapter plate 5, preferably made of carbon (carbon-fiber-reinforced polymer—CFRP) is attached to the outer side of the solidified molding element 1, in particular glued or mechanically fixed, in order to anchor markers 6 stably and reproducibly thereon. At least one pivot arm suspension 9 is preferably provided for attachment to a baseplate of an intervention or operating table 7 (cf. FIG. 7).

Figure 7:
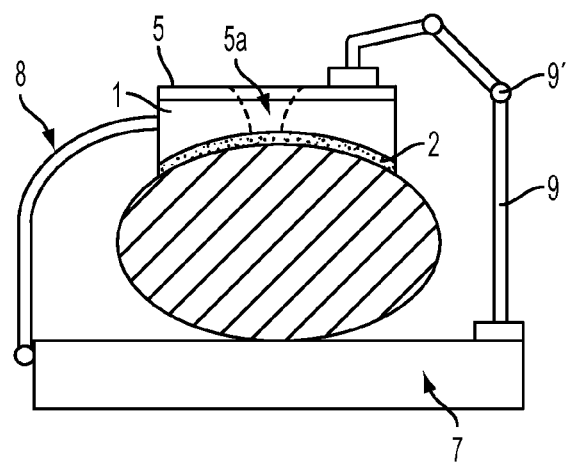
FIG. 7 is a diagram showing the use of a pivot arm with the device for immobilization; the use of a splint with the device for immobilization.

As shown in FIG. 7, the molding element 1 can have belts or tabs 8 for additional immobilization of the edge area. Diverse auxiliary devices, in particular at least one marker device 6 (see FIG. 4), can be optionally fixed on the molding element 1, preferably using at least one adapter plate 5 made of carbon, in which, as in the molding element 1 and the adhesive layer 2, an intervention opening 5a (e.g., for a puncture in the lumbar region) is provided. The pivot arm suspension 9 can additionally have at least one force or torque sensor 9', in order to detect and/or limit movements of the patient, for example, and to output a visual alarm signal in the event of excess movements. Even respiratory movements may thus be detected, so that, for example, a mini-robot for guiding a puncture needle can accordingly be sensitively driven.

Figure 8:
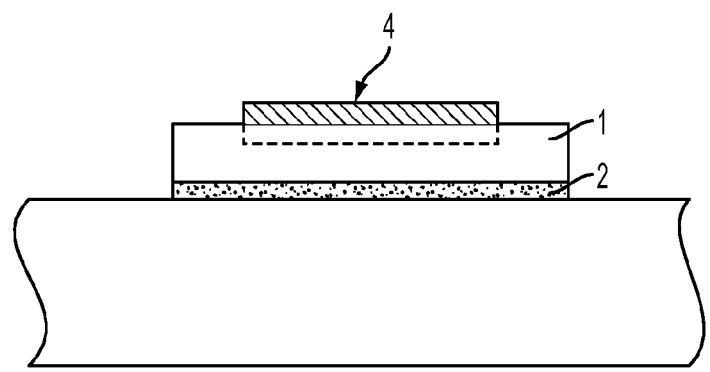
FIG. 8 is a diagram showing the use of a splint to increase the stiffness of the molding element of the device for immobilization.
Figure 9:
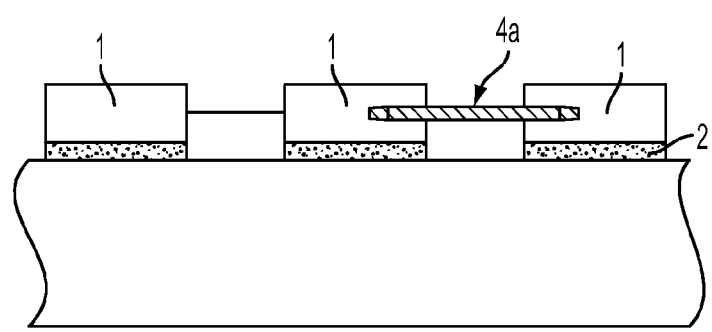
FIG. 9 is a diagram showing the use of multiple interconnected molding elements.

As shown in FIG. 8, the device, which is implemented as a vacuum cushion having a vacuum valve 3, can externally have at least one splint 4, in particular made of CFRP to increase the stiffness, on (or in) the molding element 1. This design is particularly suitable for application to arms or legs. Multiple molding elements 1 may be situated spaced apart from one another on the back or a leg, for example, and preferably can be connected to one another via tension-resistant connecting elements 4a (cf. FIG. 9). Corresponding operation areas may thus be exposed. In the case of large-area devices (cf. FIG. 3 covering the entire back area), the molding element 1 and the adhesive layer 2 have an operating or intervention opening 5a on at least one point. The molding elements 1 may be designed as L-shaped, C-shaped, or like a rectangular frame having a rectangular or preferably circular passage at the operating point, for example.

The attending physician or other persons performing treatment can therefore mold and immobilize practically any body region (entire body or only body parts) as needed. Different adapter plates and operating room window sizes further increase the flexibility. An arbitrary connection to operating tables and simple adaptation of surgical appliances and markers thus results.

The following are additionally usable as part of the invention:

upholstery between adhesive layer and molding element (increasing the comfort);

porous adhesive layer and air-conducting intermediate element allow the skin to breathe (evaporation of sweat and therefore better hold); and cooling/heating of the molding element and therefore possible therapeutic effect in the case of back/joint pains, for example.

Novel methods for the fixation/immobilization/splinting of bodies (body parts), in particular of the human body using such a molding element 1 having at least one adhesive layer 2, which is attached by adhesive forces to the body surface, are therefore made possible overall. Since the molding element 1 having adhesive layer 2 is attached to the body by adhesive forces, the encompassed/enclosed body is compressed and/or exactly (re-)positioned using defined pressure. Therefore, in the case of open wounds or cut injuries, optimal application to the wound edges and formation of a "rigid" wound bandage (less scarring, better healing) is also achieved.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A device for immobilization of the human body or of attached body parts, for attaching medical target devices, markers, or surgical instruments for image-guided, minimally invasive operations, the device comprising:

at least one molding element being filled with granules or beads and having both a moldable and a dimensionally-stable state, the at least one molding element being positionable on a body surface, wherein the at least one molding element includes a pivot arm suspension comprising at least one force or torque sensor and wherein the pivot arm suspension fixes the device to an intervention or operating table;

at least one adhesive layer disposed on the molding element to maintain contact between the body surface and the molding element;

at least one adapter plate for attaching at least one marker device to said molding element; and at least one intervention opening through the molding element, the at least one intervention opening providing access to the body surface for surgical instruments, wherein the at least one intervention opening also passes through the adapter plate and the at least one adhesive layer, and wherein the molding element is convertible from the moldable state to the dimensionally-stable state by applying a vacuum to the molding element.

2. The device according to claim 1, wherein the molding element comprises a vacuum cushion having a vacuum valve.

3. The device according to claim 1, wherein the adhesive layer comprises an inner adhesive film, a carrier layer, and an outer adhesive film.

4. The device according to claim 1, wherein an envelope of the molding element comprises a fabric or a film.

5. The device according to claim 1, wherein the molding element is elastic in a direction of attachment and is tension-resistant in a direction transverse to the direction of attachment.

6. The device according to claim 1, wherein the molding element further comprises belts or tabs.

7. The device according to claim 1, wherein the molding element comprises at least one splint to increase stiffness.

8. The device according to claim 7, wherein the at least one splint is comprised of carbon-fiber-reinforced polymer (CFRP).

9. The device according to claim 1, further comprising multiple molding elements spaced apart from one another and connected to one another via tension-resistant connecting elements.

10. The device according to claim 1, wherein the adhesive layer is formed from a skin-compatible spray adhesive.

* * * * *